United States Patent
Serhan et al.

(10) Patent No.: US 7,682,392 B2
(45) Date of Patent: Mar. 23, 2010

(54) REGENERATIVE IMPLANTS FOR STABILIZING THE SPINE AND DEVICES FOR ATTACHMENT OF SAID IMPLANTS

(75) Inventors: Hassan Serhan, S. Easton, MA (US); Paul Mraz, Boston, MA (US); Michael Andrew Slivka, Taunton, MA (US); Mike O'Neil, W. Barnstable, MA (US)

(73) Assignee: Depuy Spine, Inc., Raynham, MA (US)

( * ) Notice: Subject to any disclaimer, the term of this patent is extended or adjusted under 35 U.S.C. 154(b) by 858 days.

(21) Appl. No.: 10/283,911

(22) Filed: Oct. 30, 2002

(65) Prior Publication Data

US 2004/0088053 A1    May 6, 2004

(51) Int. Cl.
*A61F 2/44*    (2006.01)
(52) U.S. Cl. .................................. 623/17.11
(58) Field of Classification Search ............... 606/72; 623/13.17, 13.11, 13.19, 13.2, 17.11; 627/17.11
See application file for complete search history.

(56) References Cited

U.S. PATENT DOCUMENTS

| | | | |
|---|---|---|---|
| 1,105,105 A | 7/1914 | Sherman | |
| 2,143,910 A | 1/1939 | Didusch | |
| 3,054,406 A | 9/1962 | Usher | |
| 3,272,204 A | 9/1966 | Artandi | |
| 3,463,158 A | 8/1969 | Schmitt et al. | |
| 3,513,484 A | 5/1970 | Hausner | |
| 3,710,789 A | 1/1973 | Ersek | |
| 3,741,205 A | 6/1973 | Markolfe | |
| 3,848,601 A | 11/1974 | Ma et al. | |
| 4,127,902 A | 12/1978 | Homsy | |
| 4,255,820 A | 3/1981 | Rothermel et al. | |
| 4,403,606 A | 9/1983 | Woo et al. | |
| 4,409,968 A | 10/1983 | Drummond | |
| 4,411,259 A | 10/1983 | Drummond | |
| 4,512,038 A | 4/1985 | Alexander | |
| 4,570,623 A | 2/1986 | Ellison et al. | |
| 4,599,086 A | 7/1986 | Doty | |
| 4,610,688 A | 9/1986 | Silvestrini et al. | |
| 4,633,873 A | 1/1987 | Dumican et al. | |

(Continued)

FOREIGN PATENT DOCUMENTS

DE    29 14 164 A1    10/1979

(Continued)

OTHER PUBLICATIONS

Anterior Crucitae Ligament (ACL) Reconstruction Technique, Patellar Tendon Graft, Orthopaeic Associates of Portland, Sports Medicine Center, www.orthoassociates.com/acltech.htm, Douglas W. Brown, M.D., pp. 1-9, Sep. 27, 2000.

(Continued)

*Primary Examiner*—Pedro Philogene
(74) *Attorney, Agent, or Firm*—Brian Tomko

(57) ABSTRACT

The invention comprises flat, porous, bioabsorbable implants that are conducive to tissue ingrowth at spinal implantation site, and once absorbed, leave behind a functional ligamentous structure. A preferred material is small intestinal submucosa. Also disclosed are anchoring devices for attaching said implants to the vertebral bodies.

11 Claims, 1 Drawing Sheet

U.S. PATENT DOCUMENTS

Figure 1:
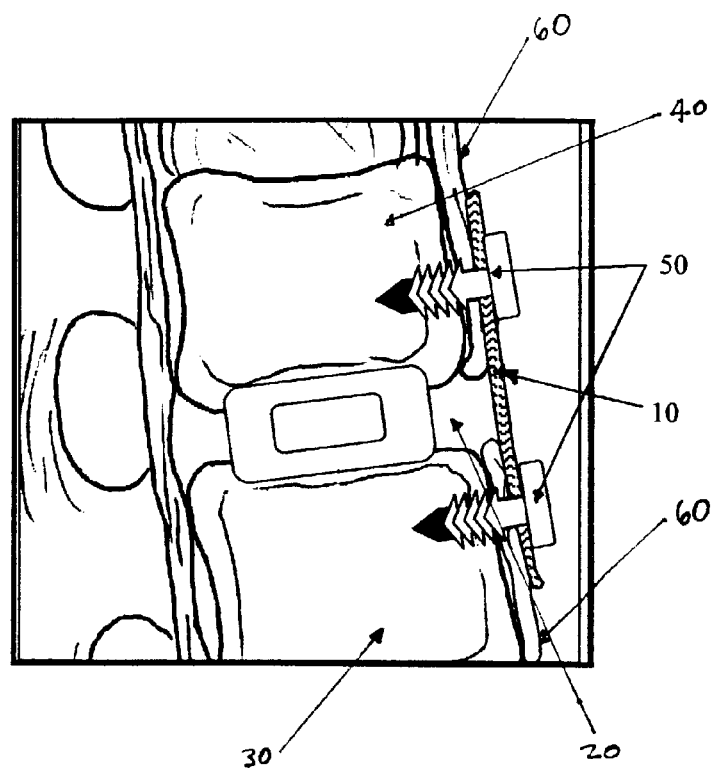

| | | |
|---|---|---|
| 4,641,636 A | 2/1987 | Cotrel |
| 4,665,951 A | 5/1987 | Ellis |
| 4,728,329 A | 3/1988 | Mansat |
| 4,743,260 A | 5/1988 | Burton |
| 4,755,183 A | 7/1988 | Kenna |
| 4,772,287 A | 9/1988 | Ray et al. |
| 4,773,406 A | 9/1988 | Spector et al. |
| 4,781,183 A | 11/1988 | Casey et al. |
| 4,792,336 A | 12/1988 | Hlavacek et al. |
| 4,815,453 A | 3/1989 | Cotrel |
| 4,820,305 A | 4/1989 | Harms et al. |
| 4,834,755 A | 5/1989 | Silvestrini et al. |
| 4,883,486 A | 11/1989 | Kapadia et al. |
| 4,902,508 A * | 2/1990 | Badylak et al. ............ 424/423 |
| 4,904,260 A | 2/1990 | Ray et al. |
| 4,905,680 A | 3/1990 | Tunc |
| 4,917,700 A | 4/1990 | Aikins |
| 4,956,178 A | 9/1990 | Badylak et al. |
| 4,987,892 A | 1/1991 | Krag et al. |
| 4,995,911 A | 2/1991 | Matsumoto et al. |
| 5,002,576 A | 3/1991 | Fuhrmann et al. |
| 5,011,484 A | 4/1991 | Breard |
| 5,013,315 A | 5/1991 | Barrows |
| 5,022,855 A | 6/1991 | Jeckel |
| 5,024,669 A | 6/1991 | Peterson et al. |
| 5,049,155 A | 9/1991 | Bruchman et al. |
| 5,074,864 A | 12/1991 | Cozad et al. |
| 5,084,049 A | 1/1992 | Asher et al. |
| 5,084,051 A | 1/1992 | Tormala et al. |
| 5,092,866 A | 3/1992 | Bread et al. |
| 5,102,421 A | 4/1992 | Anspack, Jr. |
| 5,108,395 A | 4/1992 | Laurain |
| 5,112,332 A | 5/1992 | Cozad et al. |
| 5,116,334 A | 5/1992 | Cozad et al. |
| 5,139,520 A * | 8/1992 | Rosenberg ............. 606/87 |
| 5,147,359 A | 9/1992 | Cozad et al. |
| 5,147,361 A | 9/1992 | Ojima et al. |
| 5,152,303 A | 10/1992 | Allen |
| 5,154,718 A | 10/1992 | Cozad et al. |
| 5,156,616 A | 10/1992 | Meadows et al. |
| 5,157,111 A | 10/1992 | Pachence |
| 5,171,273 A | 12/1992 | Silver et al. |
| 5,171,279 A | 12/1992 | Mathews |
| 5,180,381 A | 1/1993 | Aust et al. |
| 5,180,393 A * | 1/1993 | Commarmond ......... 623/13.14 |
| 5,197,983 A | 3/1993 | Berman et al. |
| 5,201,734 A | 4/1993 | Cozad et al. |
| 5,209,751 A | 5/1993 | Farris et al. |
| 5,222,987 A | 6/1993 | Jones |
| 5,234,431 A | 8/1993 | Keller |
| 5,242,443 A | 9/1993 | Kambin |
| 5,261,913 A | 11/1993 | Marnay |
| 5,269,783 A | 12/1993 | Sander |
| 5,281,422 A * | 1/1994 | Badylak et al. ......... 623/13.11 |
| 5,306,308 A | 4/1994 | Gross et al. |
| 5,324,290 A | 6/1994 | Zdeblick et al. |
| 5,330,473 A | 7/1994 | Howland |
| 5,344,421 A | 9/1994 | Crook |
| 5,346,492 A | 9/1994 | Morgan |
| 5,352,224 A | 10/1994 | Westermann |
| 5,352,463 A | 10/1994 | Badylak et al. |
| 5,372,821 A | 12/1994 | Badylak |
| 5,376,188 A | 12/1994 | Tahara et al. |
| 5,380,324 A | 1/1995 | Muller et al. |
| 5,380,328 A | 1/1995 | Morgan |
| 5,384,149 A | 1/1995 | Lin |
| 5,397,359 A | 3/1995 | Mittelmeier et al. |
| 5,405,391 A | 4/1995 | Hednerson et al. |
| 5,415,661 A * | 5/1995 | Holmes ............. 606/69 |
| 5,437,672 A | 8/1995 | Alleyne |
| 5,443,483 A | 8/1995 | Kirsch |
| 5,453,227 A | 9/1995 | Rieger |
| 5,456,722 A | 10/1995 | McLeod et al. |
| 5,462,478 A | 10/1995 | Fredsby |
| 5,496,372 A | 3/1996 | Hamamoto et al. |
| 5,527,311 A | 6/1996 | Procter et al. |
| 5,531,745 A | 7/1996 | Ray |
| 5,531,747 A | 7/1996 | Ray |
| 5,531,751 A | 7/1996 | Schultheiss |
| 5,534,031 A | 7/1996 | Matsuzaki et al. |
| 5,536,274 A | 7/1996 | Neuss |
| 5,540,703 A | 7/1996 | Barker, Jr. et al. |
| 5,540,964 A | 7/1996 | Mallen |
| 5,549,612 A | 8/1996 | Yapp et al. |
| 5,549,679 A | 8/1996 | Kuslich |
| 5,558,674 A | 9/1996 | Heggeness et al. |
| 5,562,736 A | 10/1996 | Ray et al. |
| 5,571,109 A | 11/1996 | Bertagnoli |
| 5,573,784 A | 11/1996 | Badylak et al. |
| 5,980,482 A | 1/1997 | Jobe |
| 5,601,554 A | 2/1997 | Howland et al. |
| 5,603,713 A | 2/1997 | Aust et al. |
| 5,609,634 A | 3/1997 | Voydeville |
| 5,616,142 A | 4/1997 | Yuan et al. |
| 5,616,144 A | 4/1997 | Yapp et al. |
| 5,628,756 A | 5/1997 | Barker, Jr. et al. |
| 5,634,926 A | 6/1997 | Jobe |
| 5,634,944 A | 6/1997 | Magram |
| 5,641,518 A | 6/1997 | Badylak et al. |
| 5,643,261 A | 7/1997 | Schafer et al. |
| 5,645,596 A | 7/1997 | Kim et al. |
| 5,647,872 A | 7/1997 | Gilbert et al. |
| 5,674,295 A | 10/1997 | Ray et al. |
| 5,674,296 A | 10/1997 | Bryan et al. |
| 5,676,666 A | 10/1997 | Oxland et al. |
| 5,676,703 A | 10/1997 | Gelbard |
| 5,681,310 A | 10/1997 | Yuan et al. |
| 5,681,311 A | 10/1997 | Foley et al. |
| 5,683,391 A | 11/1997 | Boyd |
| 5,693,099 A | 12/1997 | Harle |
| 5,702,453 A | 12/1997 | Rabbe et al. |
| 5,709,683 A | 1/1998 | Bagby |
| 5,709,686 A | 1/1998 | Talosef et al. |
| 5,711,960 A | 1/1998 | Shikinami |
| 5,711,969 A | 1/1998 | Patel et al. |
| 5,716,409 A | 2/1998 | Debbas |
| 5,721,049 A | 2/1998 | Marcolongo et al. |
| 5,728,097 A | 3/1998 | Mathews |
| 5,728,127 A | 3/1998 | Asher et al. |
| 5,735,899 A | 4/1998 | Schwartz et al. |
| 5,741,253 A | 4/1998 | Michelson |
| 5,755,791 A | 5/1998 | Whitson et al. |
| 5,766,176 A | 6/1998 | Duncan |
| 5,766,254 A | 6/1998 | Gelbard |
| 5,776,196 A | 7/1998 | Matsuzaki et al. |
| 5,785,713 A | 7/1998 | Jobe |
| 5,788,625 A * | 8/1998 | Plouhar et al. ............. 600/36 |
| 5,797,917 A | 8/1998 | Boyd et al. |
| 5,800,543 A | 9/1998 | McLeon et al. |
| 5,824,093 A | 10/1998 | Ray et al. |
| 5,846,484 A * | 12/1998 | Scarborough et al. ......... 422/28 |
| 5,857,995 A | 1/1999 | Thomas et al. |
| 5,865,846 A | 2/1999 | Bryan et al. |
| 5,868,745 A | 2/1999 | Alleyne |
| 5,876,452 A * | 3/1999 | Athanasiou et al. ...... 623/23.72 |
| 5,885,287 A | 3/1999 | Bagby |
| 5,885,619 A | 3/1999 | Patel et al. |
| 5,888,221 A | 3/1999 | Gelbard |
| 5,888,223 A | 3/1999 | Bray, Jr. |
| 5,899,902 A | 5/1999 | Brown et al. |
| 5,904,683 A | 5/1999 | Pohndorf et al. |
| 5,906,828 A | 5/1999 | Cima et al. |
| 5,919,234 A | 7/1999 | Lemperle et al. |
| 5,922,026 A | 7/1999 | Chin |

| | | | |
|---|---|---|---|
| 5,922,028 A | 7/1999 | Plouhar et al. | |
| 5,925,056 A | 7/1999 | Thomas et al. | |
| 5,955,110 A | 9/1999 | Patel et al. | |
| 5,962,427 A * | 10/1999 | Goldstein et al. | 514/44 |
| 5,968,096 A | 10/1999 | Whitson et al. | |
| 5,972,368 A | 10/1999 | McKay | |
| 5,997,575 A | 12/1999 | Whitson et al. | |
| 6,010,502 A | 1/2000 | Bagby | |
| 6,017,345 A | 1/2000 | Richelsoph | |
| 6,022,376 A | 2/2000 | Assell et al. | |
| 6,030,389 A | 2/2000 | Wagner et al. | |
| 6,031,148 A | 2/2000 | Hayes et al. | |
| 6,042,534 A | 3/2000 | Gellman et al. | |
| 6,045,552 A | 4/2000 | Zucherman et al. | |
| 6,045,554 A | 4/2000 | Grooms et al. | |
| 6,077,076 A | 6/2000 | Comfort | |
| 6,086,589 A | 7/2000 | Kuslich et al. | |
| 6,090,998 A * | 7/2000 | Grooms et al. | 128/898 |
| 6,093,205 A | 7/2000 | McLeod et al. | |
| 6,099,568 A | 8/2000 | Simonian et al. | |
| 6,113,640 A * | 9/2000 | Tormala et al. | 623/18.11 |
| 6,120,503 A | 9/2000 | Michelson | |
| 6,121,172 A | 9/2000 | Marcolongo et al. | |
| 6,127,596 A | 10/2000 | Brown et al. | |
| 6,129,730 A | 10/2000 | Bono et al. | |
| 6,136,001 A | 10/2000 | Michelson | |
| 6,136,002 A | 10/2000 | Shih et al. | |
| 6,139,550 A | 10/2000 | Michelson | |
| 6,139,551 A | 10/2000 | Michelson et al. | |
| 6,143,036 A | 11/2000 | Comfort | |
| RE37,005 E | 12/2000 | Michelson et al. | |
| 6,156,067 A | 12/2000 | Bryan et al. | |
| 6,159,213 A | 12/2000 | Rogozinski | |
| 6,162,537 A | 12/2000 | Martin et al. | |
| 6,187,009 B1 | 2/2001 | Herzog et al. | |
| 6,193,721 B1 | 2/2001 | Michelson | |
| 6,197,036 B1 | 3/2001 | Tripp et al. | |
| 6,206,881 B1 | 3/2001 | Frigg et al. | |
| 6,206,931 B1 | 3/2001 | Cook et al. | |
| 6,221,109 B1 | 4/2001 | Geistlich | |
| 6,228,085 B1 | 5/2001 | Theken et al. | |
| 6,273,889 B1 | 8/2001 | Richelsoph | |
| 6,290,703 B1 | 9/2001 | Ganem | |
| 6,293,949 B1 | 9/2001 | Justis et al. | |
| 6,296,643 B1 | 10/2001 | Hopf et al. | |
| 6,299,613 B1 | 10/2001 | Ogilvie et al. | |
| 6,302,883 B1 | 10/2001 | Bono | |
| 6,306,136 B1 | 10/2001 | Baccelli | |
| 6,306,139 B1 | 10/2001 | Fuentes | |
| 6,306,170 B2 | 10/2001 | Ray | |
| 6,312,431 B1 | 11/2001 | Asfora | |
| 6,312,474 B1 | 11/2001 | Francis et al. | |
| 6,328,738 B1 | 12/2001 | Suddaby | |
| 6,332,894 B1 | 12/2001 | Stalcup et al. | |
| 6,334,872 B1 | 1/2002 | Termin et al. | |
| 6,358,284 B1 | 3/2002 | Fearnot et al. | |
| 6,371,990 B1 | 4/2002 | Ferree | |
| 6,398,783 B1 | 6/2002 | Michelson | |
| 6,423,065 B2 | 7/2002 | Ferree | |
| 6,432,140 B1 | 8/2002 | Lin | |
| 6,440,444 B2 * | 8/2002 | Boyce et al. | 424/422 |
| 6,475,219 B1 | 11/2002 | Shelokov | |
| 6,475,232 B1 | 11/2002 | Babbs et al. | |
| 6,485,723 B1 | 11/2002 | Badylak et al. | |
| 6,497,726 B1 * | 12/2002 | Carter et al. | 623/13.17 |
| 6,554,852 B1 | 4/2003 | Oberlander | |
| 6,562,073 B2 | 5/2003 | Foley | |
| 6,576,017 B2 | 6/2003 | Foley et al. | |
| 6,616,694 B1 | 9/2003 | Hart | |
| 6,616,698 B2 * | 9/2003 | Scarborough | 623/23.51 |
| 6,752,831 B2 * | 6/2004 | Sybert et al. | 623/13.17 |
| 6,893,462 B2 * | 5/2005 | Buskirk et al. | 623/13.17 |
| 2001/0014807 A1 | 8/2001 | Wagner et al. | |
| 2001/0018614 A1 | 8/2001 | Bianchi | |
| 2001/0020185 A1 | 9/2001 | Ray | |
| 2001/0031254 A1 | 10/2001 | Bianchi et al. | |
| 2001/0041894 A1 | 11/2001 | Campbell et al. | |
| 2002/0007218 A1 | 1/2002 | Cauthen | |
| 2002/0010466 A1 | 1/2002 | Alleyne | |
| 2002/0013586 A1 | 1/2002 | Justis et al. | |
| 2002/0038151 A1 | 3/2002 | Plouhar et al. | |
| 2002/0045898 A1 | 4/2002 | Freid et al. | |
| 2002/0058939 A1 | 5/2002 | Wagner et al. | |
| 2002/0068975 A1 | 6/2002 | Teitelbaum et al. | |
| 2002/0072806 A1 * | 6/2002 | Buskirk et al. | 623/23.51 |
| 2002/0077630 A1 | 6/2002 | Lin | |
| 2002/0107570 A1 | 8/2002 | Sybert et al. | |
| 2002/0107571 A1 | 8/2002 | Foley | |
| 2002/0107572 A1 | 8/2002 | Foley et al. | |
| 2002/0111688 A1 | 8/2002 | Cauthen | |
| 2002/0120270 A1 | 8/2002 | Trieu et al. | |
| 2002/0120337 A1 | 8/2002 | Cauthen | |
| 2002/0123807 A1 | 9/2002 | Cauthen, III | |
| 2002/0143329 A1 | 10/2002 | Serhan | |
| 2002/0161449 A1 * | 10/2002 | Muschler | 623/23.51 |
| 2003/0036800 A1 * | 2/2003 | Meredith | 623/23.63 |
| 2003/0036801 A1 * | 2/2003 | Schwartz et al. | 623/23.63 |

FOREIGN PATENT DOCUMENTS

| | | |
|---|---|---|
| DE | 4201043 A1 | 7/1993 |
| EP | 0 050 162 B1 | 4/1986 |
| EP | 0 304 305 B1 | 5/1992 |
| EP | 0 353 936 B1 | 11/1992 |
| EP | 0542004 A1 | 5/1993 |
| EP | 0 507 162 B1 | 3/1994 |
| EP | 0599766 A1 | 6/1994 |
| EP | 0 520 177 B1 | 12/1995 |
| FR | 2 612 392 A1 | 9/1988 |
| FR | 87 044187 A1 | 9/1988 |
| FR | 2 709 410 A1 | 3/1995 |
| WO | WO 90/07304 A1 | 7/1990 |
| WO | WO 91/06249 A1 | 5/1991 |
| WO | WO 9211819 A1 | 7/1992 |
| WO | WO 93/22989 A1 | 11/1993 |
| WO | WO 94/21185 A1 | 9/1994 |
| WO | WO 98/51226 A2 | 11/1998 |
| WO | WO 98/55053 A1 | 12/1998 |
| WO | WO 99/47082 A1 | 9/1999 |
| WO | WO 99/62439 A1 | 12/1999 |
| WO | WO 00/03653 A2 | 1/2000 |
| WO | WO 00/59388 A1 | 10/2000 |
| WO | WO 00/64365 A1 | 11/2000 |
| WO | WO 00/72782 A1 | 12/2000 |
| WO | WO 02/056800 A2 | 7/2002 |

OTHER PUBLICATIONS

Anterior Cruciate Ligament (ACL) Graft Options, Orthopaedic Associates of Portland, Sports Medicine Center, www.orthoassociates.com/acl-grafts.htm, F. Lincoln Avery, M.D., pp. 1-10, Sep. 27, 2000.

PCL Reconstruction: Fixation Techniques; Wheeles' Textbook of Orthopaedics; www.medmedia.com/012/5000.htm, Sep. 27, 2000, p. 1 of 1.

Arthroteck Product Information, www.arthroteck.com and product literature; Sep. 27, 2000.

McKenzie, Alvin H., MD, :Remoteflow Intervertebral Disc Arthroplasty: A Long-Term Evaluation, Ortrhopaedics International Edition, vol. 3, No. 4, pp. 313-324, Jul./Aug. 1995.

Grevitt, M.P., "The Graf Stabilisation System: Early Results in 50 Patients", European Spine Journal, 1995; 4(3), pp. 169-175.

Presentation entitled *"Effectiveness of Small Intestine Submucosa (SIS) for Spinal Ligament Repair"*, made at the North American Spine Society Meeting on Nov. 2, 2001 at Seattle, Washington.

Ledet, Eric H. et al., "*A Pilot Study to Evaluate the Effectiveness of Small Intestinal Submucosa used to Repair Spinal Ligaments in the Goat*" The Spine Journal 2, May/Jun. 2002, pp. 188-196, vol. 2, No. 3.

Carl, A.L. et al., Abstract "*The Effectiveness of SIS for Spinal Ligament Repair in the Goat*," North American Spine Society, North American Spine Society Proceedings, 16$^{th}$ Annual Meeting, Washington State Convention and Trade Center, Seattle, Washington, Oct. 31-Nov. 3, 2001, pp. 77-78.

U.S. Appl. No. 60/181,622, Bianchi et al.

U.S. Appl. No. 60/296,530, Wironen et al.

U.S. Appl. No. 60/181,622, filed Feb. 10, 2000, J. Bianchi et al.

U.S. Appl. No. 60/296,530, filed Jun. 6, 2001, J. Wironen et al.

Neuroschirurgie 1994;40(3):196-200.

Spine Mar. 1, 1994;19(5);550-5.

Spine Jun. 1, 1994;19(11);1271-9;discussion 1280.

English Abstract, EP054004, Publication Date: May 19, 1993, Applicant: Howmedica GmbH.

English Abstract, DE4201043, Publication Date: Jul. 22, 1993, Applicant: Ulrich, Heinrich.

\* cited by examiner

REGENERATIVE IMPLANTS FOR STABILIZING THE SPINE AND DEVICES FOR ATTACHMENT OF SAID IMPLANTS

FIELD OF THE INVENTION

This invention is directed to implants and attachment devices for said implants directed toward stabilizing the spine following surgical procedures and that encourage regeneration of a natural anterior longitudinal ligament and interspinous ligaments replacement.

BACKGROUND

Destabilization of the lumbar spine results from sacrifice of the anterior longitudinal ligament and disc when removed for graft or cage placement. Similarly, transection of the interspinous ligaments during surgical approaches to the posterior spine may result in instability. Such instability may cause abnormal motion or implant migration resulting in a high incidence of pseudarthrosis.

In anterior interbody surgical procedures, the anterior longitudinal ligament is sacrificed, resulting in instability which can lead to hyperextension and interbody device migration.

Current anterior spinal interbody fusion procedures are performed either standalone, using a buttress plate or using anterolateral or posterior rigid fixation. Interbody motion devices are implanted without augmenting the device, since no device is available that can provide stability and containment yet allow for normal range of motion. This is a particularly challenging problem when dealing with the normal range of movement of the spine.

U.S. Pat. No. 5,681,310 "Yuan" discloses a holding mat for preventing a foreign object from jutting out of the vertebra. The mat is attached using a plurality of fastening elements and all components are capable of being assimilated into the tissues of a human body. However, the device is not specifically designed to facilitate regeneration of a mechanically appropriate repair tissue, but only to contain foreign objects within the vertebra.

U.S. Pat. No. 6,371,990, "Ferree", discloses a flexible, biocompatible material that is attached to adjacent vertebral bodies for the purpose of fortifying the annulus fibrosis. The device is used in conjunction with a device for covering the inner wall of the annulus. Ferree discloses using treated pig intestine combined with the invention to promote tissue ingrowth. However, the device is not specifically designed to facilitate regeneration of a mechanically appropriate repair tissue.

U.S. Pat. No. 6,221,109, "Geistlich", discloses a collagen membrane wrapped around the vertebrae and disc for protection of the spinal cord from implants jutting out of the disc space. The device is used in conjunction with a collagen membrane wrapped around the spinal cord. The device is not specifically designed to facilitate regeneration of a mechanically appropriate repair tissue and appears to be limited to the posterior aspect of the spine surrounding the spinal cord.

U.S. Pat. No. 6,093,205, "McLeod", discloses a fabric element attached to adjacent vertebrae for the purpose of retaining a specific disc prosthesis described in the invention. The fabric may be made of a resorbable material and may have structure and/or properties to encourage tissue ingrowth. The fabric may be attached using sutures, staples, and bone screws. The device is not specifically designed to facilitate regeneration of a mechanically appropriate repair tissue and is disclosed as an integral part of the disc prosthesis described.

U.S. Pat. No. 5,372,821, "Badylak", discloses a method for promoting autogenous regrowth of damaged or diseased ligaments by attaching small intestinal submucosa. No mention is made to spinal ligaments, attachment thereof to the spine, or as an augmentation to an intervertebral disc surgical therapy. Similarly, U.S. Pat. No. 5,922,028, "Plouhar", discloses a tissue graft construct for repairing or replacing a cartilaginous structure located between two bones comprising small intestinal submucosa with 50 to 200 layers and thickness of 4-8 mm and sculpted to the proper shape. Although the patent refers to reconstructing the intervertebral disc, no mention is made to regenerating the spinal ligaments, to achieving a mechanically appropriate repair tissue, or as an adjunct to an intervertebral disc surgical therapy.

Thus there is a need in the art for bioabsorbable, anterior longitudinal ligament and interspinous ligament replacement implants that serve to restore stability following surgical removal of the native ligaments, contain intervertebral body devices or grafts, and encourage regeneration of a functional repair tissue for long-term stability such as described in this invention.

BREIF DESCRIPTION OF THE DRAWINGS

Figure 2:
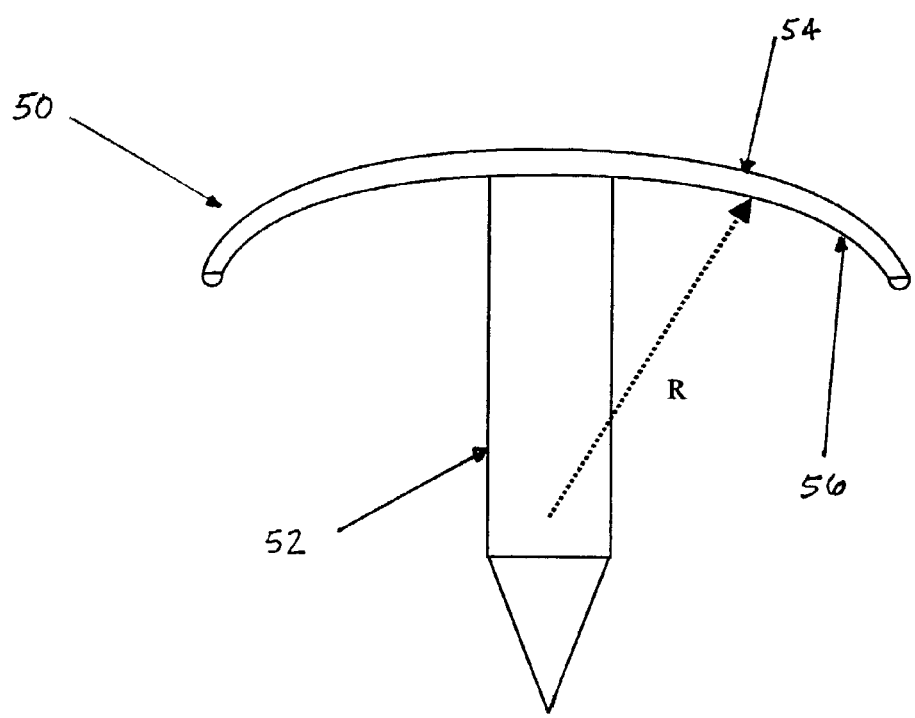

The invention will be more fully understood from the following detailed description taken in conjunction with the accompanying drawings, in which:

FIG. 1 depicts use of the implant of the invention for forming a natural spinal ligament; and FIG. 2 depicts a suitable anchor device for the invention.

SUMMARY OF THE INVENTION

One aspect of this invention relates to a method for promoting autogenous regrowth and healing of resected, damaged or diseased spinal ligaments comprising the step of surgically repairing said structures by securing one end of an implant to a first spinal vertebrae, transversing the intervertebral space and securing a second end of the implant to a second vertebra, said implant formed from a material that encourages regeneration of a ligament or tendon replacement.

Another aspect of this invention relates to a spinal ligament or tendon implant comprising a material that encourages regeneration of a ligament or tendon.

Yet a further aspect of the invention relates to an anchoring device which a flexible head having a radius of curvature that insures intimate contact between the implant and the tissue that the implant is being attached to.

DETAILED DESCRIPTION OF THE INVENTION

The disclosed invention serves a multitude of purposes for augmenting interbody device implantation for the spine, including: 1) providing initial stability to motion segment, 2) preventing interbody device migration by means of both a physical barrier and as a tension band, and 3) having a physical and chemical structure conducive to assisting the body in regenerating a mechanically appropriate repair tissue.

Devices of the proposed invention are preferably porous, thereby acting as a scaffold for cells to occupy and produce extracellular matrix. The cells may migrate from the surroundings following implantation or be seeded onto the porous device prior to implantation. Alternatively, the cells may be cultured on the porous device for a period of time prior to implantation. Alternatively, bioactive factors may be adsorbed onto or absorbed into the porous device prior to implantation.

Examples of suitable cells include cells harvested from ligaments in the body. Preferably, the cells are obtained from spinal ligaments such as the anterior longitudinal ligament and the posterior interspinous ligaments. Other examples include but are not limited to: stem cells, fibrocytes, adipocytes and chondrocytes.

Examples of suitable bioactive factors include but are not limited to transforming growth factor-beta and agents in the same family of growth factors, platelet-derived growth factors, fibroblast growth factors, insulin-like growth factors, protein polymers such as RGD-peptides and Indian Hedgehog proteins, anti-inflammatory agents, hormones, hyaluronic acid and the like.

Implants of the proposed invention are also preferably susceptible to breaking down after implantation, thereby acting as a temporary support structure for tissue regeneration and resulting in a primarily native repair tissue structure. Preferably the breakdown products of the invention are easily processed by the body through normal metabolic pathways.

Preferred materials of this invention include collagen, hyaluronic acid, elastin, synthetic polymers such as polylactide, polyglycolide and copolymers thereof. In one preferred embodiment of this invention, the porous device is a textile structure comprised of drawn fibers of the aforementioned materials. In a more preferred embodiment, the fibers are woven or braided into the appropriate scaffold structure mentioned.

A preferred collagen material of this invention is small intestinal submucosa (SIS) which is a naturally occurring extracellular collagen based matrix. SIS is described in detail in U.S. Pat. No. 5,372,821, the disclosure of which is hereby incorporated by reference. As described in the '821 patent, SIS is a segment of intestinal tissue of a warm-blooded vertebrate, said segment comprising the tunica submucosa and basilar tissue of the tunica mucosa, said tunica submucosa and basilar tissue being delaminated from the tunica muscularis and the luminal portion of the tunica mucosa of said segment of intestinal tissue. SIS contains cytokines and growth factors and has been shown to act as a resorbable scaffold in vivo which promotes soft tissue regeneration with little scar tissue formation. SIS can be manufactured in laminated sheets of various sizes and thicknesses for different indications. Successful applications of SIS have included: dural substitution, rotator cuff repair, tendinosis, vessel repair, abdominal and bladder wall repair, and others. However, prior to investigations initiated and directed by the inventors, SIS is not known to have been investigated to determine its ability to facilitate regeneration of spinal ligaments.

We have found that the strength of the spinal ligament is controlled by the layering of the SIS. For example, we have performed tensile testing to show that by orienting all layers of the SIS patch in the same direction, a higher ultimate strength can be achieved. When 20 layers were stacked up changing the orientation 72° with each layer ("isotropic"), the ultimate tensile strength was 282 N for a 20 mm wide patch. When all 20 layers were stacked with the same orientation and tested in the direction of higher strength, the ultimate strength was 353 N. Thus the number and orientation of the layers may be adjusted to achieve various tensile strengths depending on the vertebrae to be attached. For example, tensile strengths of 10 N for cervical, 300 N for thoracic, and 450 N for lumbar ligaments are achievable.

The invention may be applied to the spine using any one or more of a variety of attachment means. Such attachment means include but are not limited to adhesives, sutures, suture anchors, soft tissue anchors, staples, and screw/washer systems. In a preferred embodiment of this invention, the device is attached to the anterior aspect of adjacent level vertebral bodies following surgical treatment of the intervertebral space. Thus referring to FIG. 1, implant 10 is shown to bridge the intervertebral space 20 which lies between vertebral body 30 and vertebral body 40. Anchor devices 50 are shown to penetrate implant 10 and vertebral bodies 30 and 40, respectively. In a preferred embodiment, existing spinous ligament tissue 60 is intimately contacted with implant.

In another aspect of this invention, the anchoring devices 50 include as part of their design a head that comes in intimate contact with implant 10 upon final seating of the anchor device 50. FIG. 2 shows a schematic representation of one embodiment of the anchor design. Referring to FIG. 2, anchor device 50 comprises shaft 52 and head 54. Head 54 preferably has a radius of curvature (R) and flexibility such that upon final anchoring, implant 10 is compressed substantially between head 54 of the anchor and the vertebral body. In another more preferred embodiment, the underside surface 56 of head 54 in contact with implant 10 includes grooves or a roughened pattern to increase holding strength.

EXAMPLE

The following example demonstrates the efficacy of SIS to restore stability in the spine and to act as a scaffold for regeneration of the anterior longitudinal ligament (ALL) and interspinous ligaments (ISL) in a goat model.

Four skeletally mature nubian-alpine cross-bred goats were used in this study. Under general anesthesia, each $T_{10}$ to $L_5$ motion segment was exposed surgically. Both an anteriolateral and posterior approach were made at each level.

Anteriorly, every other level received either: anterior discectomy, sacrifice of ALL, and placement of SIS; anterior discectomy, sacrifice of ALL, and no SIS ("Control"); or sham operation ("Sham"). A solid interbody spacer was placed into the disc space at each SIS and control level to prohibit spontaneous anterior interbody fusion. A sheet of SIS was applied to the ventral surface of each SIS level such that it spanned the disc space making intimate contact with the remaining ALL superiorly and inferiorly. The SIS was secured to the cranial and caudal vertebral bodies with bone staples, suture anchors, and suture.

Posteriorly, every other level received either: sacrifice of the ISL with placement of SIS ("SIS"); sacrifice of ISL and no SIS ("Control"); or sham operation ("Sham"). At SIS levels, a sheet of SIS was applied dorsal to the spinous processes and wrapped over the left and right lateral aspect. The SIS was secured to the spinous processes with suture anchors. Sutures were passed through the SIS and around the adjacent spinous processes to create a tension-band effect.

Animals were radiographed immediately post-operatively to confirm implant placement and to serve as a baseline for interbody spacer positioning. Following surgery, all animals were allowed unrestricted motion for twelve weeks. At the end of the twelve week period, animals were radiographed and euthanized.

The lumbar spine was harvested en bloc and processed for decalcified histologic evaluation. The dorsal and ventral aspects of each motion segment were analyzed for signs of inflammation and scar tissue formation, residual SIS, and regenerated ALL or ISL.

The results showed that animals tolerated the surgical procedure well and there were no intraoperative or anesthesia related complications. Immediate post-operative radiographs showed proper placement of all implants.

Gross analysis at necropsy indicated iatrogenic scar formation, the degree of which was not different from controls to SIS levels. Histologic evaluation of areas where the ALL had been removed indicated formation of organized fibrillar collagenous tissue which spanned the disc space at some levels where the SIS was placed. The newly formed tissue was approximately 70% the thickness of the ALL at the sham level. The newly formed collagenous tissue was accompanied by sparse focal areas of inflammation and no residual SIS at some levels. At control levels, there was limited formation of sparsely organized connective tissues. At sham levels, normal ligamentous structures were present. Similarly, histologic analysis of some levels where SIS was placed posteriorly showed formation of organized collagenous tissues where the ISL had been removed.

Thus, placement of the SIS resulted in regeneration of the ligamentous-like tissues in the spine to a varying degree with limited signs of inflammation and scar formation. This result indicates the potential for SIS in repair of spinal ligaments for restabilization of the lumbar spine.

The invention claimed is:

1. A method for promoting autogenous regrowth and healing of resected, damaged or diseased spinal ligaments comprising the steps of:

surgically repairing a spinal ligament by securing a first end of an implant to a first vertebra, transversing the intervertebral space and securing a second end of the implant to a second vertebra, said implant being formed from a material that encourages regeneration of a ligament or tendon replacement;

wherein the material is formed from a segment of intestinal tissue of a warm-blooded vertebrate, said segment comprising one of the tunica submucosa and basilar tissue of the tunica mucosa, said tunica submucosa and basilar tissue being delaminated from the tunica muscularis and the luminal portion of the tunica mucosa of said segment of intestinal tissue; and wherein the step of securing the first end of the implant to a first vertebra comprises attaching the first end of the implant to a portion of an existing spinous ligament tissue and the first vertebra.

2. The method of claim 1, wherein the spinal ligament is an anterior longitudinal ligament.

3. The method of claim 1, wherein the spinal ligament is an interspinous ligament.

4. The method of claim 1, wherein the attaching step comprises penetrating a distal end of an anchor through the first end of the implant, through the portion of the existing spinous ligament tissue and into the first vertebra.

5. The method of claim 4, wherein the anchor has a head and the attaching step comprises the step of contacting the first end of the implant with the head of the anchor.

6. The method of claim 4, further comprising the step of compressing the first end of the implant between the anchor and the first vertebra.

7. The method of claim 1, wherein the attaching step comprises attaching the first end of the implant to an anterior aspect of the first vertebra.

8. The method of claim 1, wherein the attaching step comprises the step of contacting the portion of the existing spinous ligament tissue with the first end of the implant.

9. The method of claim 1, wherein the portion of the existing ligament is a resected end of the resected, damaged or diseased spinal ligament.

10. The method of claim 4, wherein the step of securing the second end of the implant to a second vertebra comprises attaching the second end of the implant to a portion of an existing spinous ligament tissue and the second vertebra.

11. The method of claim 10, wherein the attaching step comprises penetrating a distal end of a second anchor through the second end of the implant, through the portion of the existing spinous ligament tissue and into the second vertebra.

* * * * *